United States Patent
Chen et al.

(10) Patent No.: US 11,291,619 B2
(45) Date of Patent: Apr. 5, 2022

(54) WATER RESISTANCE SUNSCREEN COMPOSITIONS

(71) Applicant: L'OREAL, Paris (FR)

(72) Inventors: Yingchao Chen, Scotch Plains, NJ (US); Anil Shah, Hamilton, NJ (US); Brian Bodnar, Manasquan, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/722,743

(22) Filed: Dec. 20, 2019

(65) Prior Publication Data
US 2021/0186848 A1 Jun. 24, 2021

(51) Int. Cl.
| | | |
|---|---|---|
| *A61K 8/87* | (2006.01) | |
| *A61K 8/92* | (2006.01) | |
| *A61K 8/06* | (2006.01) | |
| *A61Q 17/04* | (2006.01) | |
| *A61K 8/362* | (2006.01) | |
| *A61K 8/36* | (2006.01) | |
| *A61K 8/88* | (2006.01) | |

(52) U.S. Cl.
CPC .............. *A61K 8/87* (2013.01); *A61K 8/062* (2013.01); *A61K 8/361* (2013.01); *A61K 8/362* (2013.01); *A61K 8/88* (2013.01); *A61K 8/92* (2013.01); *A61K 8/922* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 10,543,161 B1 * | 1/2020 | Farran | A61K 8/87 |
| 2014/0186411 A1 * | 7/2014 | Shah | A61K 8/891 |
| | | | 424/401 |
| 2018/0263866 A1 * | 9/2018 | Deckner | A61K 8/25 |

* cited by examiner

*Primary Examiner* — Kyung S Chang
(74) *Attorney, Agent, or Firm* — Laetitia Leproust; Robert Klemz

(57) ABSTRACT

An oil-in-water cosmetic composition is provided. The composition includes an oil-in-water wherein the emulsion includes a) at least one film former, b) at least one oil phase thickener, c) an emulsifying system, d) one or more organic UV filters. The oil-in-water cosmetic composition is water resistant.

13 Claims, No Drawings

WATER RESISTANCE SUNSCREEN COMPOSITIONS

FIELD OF THE DISCLOSURE

The instant disclosure is directed to water resistance sunscreen compositions, and to methods for using the sunscreen compositions to protect keratinous substrates such as skin and hair from UV radiation.

BACKGROUND

The need for compositions for imparting water resistance and aiding retention of active ingredients in personal care compositions is well known. Without them, personal care actives may wash off, wear off, be re-emulsified, or otherwise lose their efficacy. The problem with current water resistance imparting polymers is they are typically very tacky and impart bad aesthetic feel to consumers when formulated into leave-on formulations. For reference, aesthetics is one of the most important considerations in a consumer's selection of, or at least loyalty to, a personal care composition. Accordingly, what is needed is a water resistance composition polymer which possesses improved aesthetic performance, as well as excellent retention of active ingredients when water is present. The inventors of the instant disclosure discovered a novel way to boost water resistance while maintaining high SPF by combining certain type of film formers with certain type of oil phase thickeners.

SUMMARY OF THE DISCLOSURE

The instant disclosure relates to sunscreen compositions which provide a high degree of sun protection, are aesthetically pleasing when applied to skin, and are water resistant.

The inventors of the instant case discovered a combination of ingredients within a certain ratio that improve the feeling, aesthetic, SPF, and water resistance of the compositions. The sunscreen compositions in the form of an oil-in-water cosmetic composition typically include:
  a. From about 1 to about 5 wt. % of at least one film former;
  b. From about 0.2 to about 2 wt. % of at least one oil phase thickener;
  c. An emulsifier system comprising:
    i. At least one anionic surfactant
    ii. At least one nonionic surfactant having an HLB of greater than or equal to about 14.0; and
    iii. At least one nonionic surfactant having an HLB from about 1.0 to about 5.0.
  wherein the combined HLB of the surfactants is from about 9.0 to about 13.0;
  d. one or more organic UV filters;
wherein the combination of the film former and the oil phase thickener improves the water resistance of the composition, improves the SPF of the composition, and provides a good sensorial once applied on the skin; and wherein the weight percentages are based on the total weight of the composition.

Said at least one film former may be a polyurethane latex polymer, for example, those that are prepared using an emulsification polymerization process, including for example, aqueous polyurethane dispersions and other waterbourne polymers. Non-limiting examples include polyurethane 32, polyurethane-34, polyurethane-35, polyurethane-48, and mixtures thereof. In some cases, the at least one film former is present from about 1 to about 5 wt. % based on the total weight of the composition.

In some embodiments, the at least one oil phase thickener is a polyamide resin. In various embodiments, the polyamide resin is terminated with an ester, an amide, a polyalkyleneoxy group, or mixtures thereof. In some embodiments, the polyamide resin is terminated with an ester. In one or more embodiments, the at least one oil phase thickener is chosen from Ethylenediamine/Stearyl Dimer Dilinoleate Copolymer, Hydrogenated Castor Oil, Synthetic Oils, Hydrogenated Palm Oil, Hydrogenated Coconut Oil, waxes, and mixtures thereof. In some embodiments, the at least one oil phase thickener is Ethylenediamine/Stearyl Dimer Dilinoleate Copolymer. In one embodiments, the at least one oil phase thickener is Hydrogenated Castor Oil. In some embodiments, the oil phase thickener is about 0.2 to about 2.5 wt. % based on the total weight of the composition.

In some embodiments, the at least one anionic surfactant is chosen from alkali metal salts of monoalkyl or dialkyl esters of phosphoric acid, such as potassium cetyl phosphate, dicetyl phosphate, and dimyristyl phosphate; alkali metal salts of cholesterol esters of sulphonic and phosphoric acid, such as cholesterol sulphate and cholesterol phosphate; lipoamino acids and their salts; alkali metal salts of phosphatidic acid; phospholipids; alkylsulphonic derivatives; and mixtures thereof. In one or more embodiments, the lipoamino acids and their salts are chosen from sodium stearoyl glutamate and disodium stearoyl glutamate. In some embodiments, the at least one anionic surfactant is potassium cetyl phosphate.

In some embodiments, the at least nonionic surfactant having an HLB of greater than or equal to about 14.0 is chosen from Polyoxyethylene fatty acid esters and mixture thereof. In one embodiment, the polyoxyethylene fatty acid esters is PEG-100 Stearate.

In various embodiments, the at least one nonionic surfactant having an HLB from about 1 to about 5 is chosen from Glycol Distearate (HLB=1), Sorbitan Trioleate (HLB=1.8), Propylene Glycol Isostearate (HLB=2.5), Glycol Stearate (HLB=2.9), Sorbitan Sesquioleate (HLB=3.7), Glyceryl Stearate (HLB=3.8), Lecithin (HLB=4), Sorbitan Oleate (HLB=4.3), Sorbitan Monostearate NF (HLB=4.7), Sorbitan Stearate (HLB=4.7), Sorbitan Isostearate (HLB=4.7), Steareth-2 (HLB=4.9), and Oleth-2 (HLB=4.9) and mixtures thereof. In one embodiment, the at least one nonionic surfactant having an HLB from about 1.0 to about 5.0 is Glyceryl Stearate.

In one or more embodiments, the combined HLB of the surfactants is from about 9.0 to about 13.0.

In some embodiments, the sunscreens compositions may, further, include emollients. In one or more embodiments, the emollients are chosen from Diisopropyl Sebacate, Butyrospermum Parkii (Shea) Butter/Butyrospermum Parkii Butter, C12-15 Alkyl Benzoate, and mixture thereof.

Non-limiting examples of organic UV filters include para-aminobenzoate derivative, a salicylate derivative, a cinnamate derivative, a benzophenone or an aminobenzophenone derivative, an anthranillate derivative, a β,β-diphenylacrylate derivative, a benzylidenecamphor derivative, a phenylbenzimidazole derivative, a benzotriazole derivative, a triazine derivative, a bisresorcinyl triazine derivative, an imidazoline derivative, a benzylmalonate derivative, a 4,4-diarylbutadiene derivative, a benzoxazole derivative, a merocyanine derivative, a malonitrile or a malonate diphenyl butadiene derivative, a chalcone derivative, and mixtures thereof. It is common to include a plurality of organic UV filters, i.e., two or more organic UV filters. It is also useful to include at least one organic UVA filter (e.g., avobenzone) and at least one organic UVB filter.

In some embodiments, the one or more organic UV filters is present from about 1 to about 40 wt. % based on the total weight of the composition.

In some embodiments, may comprise:
a. From about 1 to about 5 wt. % of at least one film former chosen from polyurethane 32, polyurethane-34, polyurethane-35, polyurethane-48, and mixtures thereof;
b. From about 0.5 to about 1.5 wt. % of at least one oil phase thickener chosen from Ethylenediamine/Stearyl Dimer Dilinoleate Copolymer, Hydrogenated Castor Oil, Synthetic Oils, Hydrogenated Palm Oil, Hydrogenated Coconut Oil, waxes and mixtures thereof;
c. An emulsifier system comprising:
  i. From about 0.1% to about 2% of at least one anionic surfactant;
  ii. From about 0.5% to about 2% of at least one nonionic surfactant having an HLB of greater than or equal to about 14.0; and
  iii. From about 0.5% to about 2% of at least one nonionic surfactant having an HLB from about 1.0 to about 5.0; and
d. one or more organic UV filters;
wherein the combination of the film former and the oil phase thickener improves the water resistance of the composition, improves the SPF of the composition and provides a good sensorial once applied on the skin; and wherein the weight percentages are based on the total weight of the composition.

In one or more embodiments, the oil-in-water cosmetic composition has an SPF of 15 to 100. In one embodiment, the oil-in-water cosmetic composition has an SPF of 15 to 50.

In some embodiments, the compositions disclosed in the instant disclosure is water resistant.

The instant disclosure also relates to methods for protecting skin or hair from UV radiation comprising applying an effective amount of the oil-in-water composition disclosed in the instant case to the skin or hair.

Without being bound by theory or mechanism, it is suggested that the water resistance of the oil-in-water composition disclosed in the instant case is a result of the particular ratio of film former to oil-thickener, given the specific emulsification system, wherein the film former yields improved adherence to the skin and the oil thickener yields improved cohesiveness of the oil phase and sunscreens in the deposit.

It is to be understood that both the foregoing general description and the following detailed description are exemplary and explanatory only, and are not restrictive of the invention.

DETAILED DESCRIPTION OF THE DISCLOSURE

The oil-in-water compositions of the instant disclosure, in their broadest sense, typically include the following:
a. From about 1 to about 5 wt. % of at least one film former;
b. From about 0.2 to about 2 wt. % of at least one oil phase thickener;
c. An emulsifier system comprising:
  i. At least one anionic surfactant
  ii. At least one nonionic surfactant having an HLB of greater than or equal to about 14.0; and
  iii. At least one nonionic surfactant having an HLB from about 1.0 to about 5.0; and
wherein the combined HLB of the surfactants is from about 9.0 to about 13.0;
d. one or more organic UV filters;
wherein the combination of the film former and the oil phase thickener improves the water resistance of the composition, improves the SPF of the composition and provides a good sensorial once applied on the skin; and wherein the weight percentages are based on the total weight of the composition.

In addition to the organic UV filters and the cosmetically acceptable carrier, the sunscreen composition may optionally include fatty compounds, nonionic emulsifiers, water-soluble solvents, etc.

Film Formers

The oil-in-water cosmetic composition include at least one film former.

Non-limiting examples of useful film formers include a polyurethane latex polymers, for example, those that are prepared using an emulsification polymerization process, including for example, aqueous polyurethane dispersions. Non-limiting examples include polyurethane 32, polyurethane-34, polyurethane-35, polyurethane-48, and mixtures thereof. In some cases, the at least one film former is present from about 1.0 to about 3.5 wt. % based on the total weight of the composition.

The total amount of film formers in the cosmetic composition can vary but is typically about 1 to about 3.5 wt. %, based on the total weight of the composition. In some cases, the total amount of film formers can be from about 1.0, 1.2, 1.4, 1.5, 1.6, 1.7, 1.8, 1.9, 2.0 to about 2.0, 2.1, 2.2, 2.3, 2.4, 2.5, 2.6, 2.7, 2.8, 2.9, 3.0, 3.1, 3.2, 3.3, 3.4 or 3.5 wt. %, based on the total weight of the composition.

Oil Phase Thickeners

The oil phase thickeners used in the present disclosure can be selected from semi-crystalline or crystalline polymers and/or semi-crystalline or crystalline waxes.

Semi-Crystalline or Crystalline Polymer

The cosmetic composition of the invention includes at least one semi-crystalline polymer.

The term "semi-crystalline polymer" is used to mean polymers having a crystallizable portion, a crystallizable pendant chain, or a crystallizable sequence in its backbone, and an amorphous portion in the backbone, and that also presents a first-order reversible change-of-phase temperature, in particular for melting (solid-liquid transition). When the crystallizable portion is in the form of a crystallizable sequence of the polymer backbone, the amorphous portion of the polymer is in the form of an amorphous sequence. The semi-crystalline polymer is then a sequenced copolymer, e.g. of the diblock, triblock, or multiblock type, having at least one crystallizable sequence and at least one amorphous sequence. The term "sequence" generally means at least five identical repetition motifs. The crystallizable sequence(s) is/are then of a chemical nature that is different from the amorphous sequence(s).

The semi-crystalline polymer has a melting temperature greater than or equal to 30 degrees centigrade, in particular lying in the range 30 degrees centigrade to 100 degrees centigrade, preferably in the range 30 degrees centigrade to 80 degrees centigrade. The melting temperature is a first-order change-of-state temperature.

This melting temperature may be measured by any known method, and in particular by using differential scanning calorimetry (DSC).

Additionally, the semi-crystalline polymer applicable in this invention has molecular weight (MW) from about 30,000 (g/mol) to about 200,000 (g/mol).

The at least one semi-crystalline polymer may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges there between.

By way of examples, such polymers are described in EP 1 396 259 and U.S. Pat. No. 8,980,240, the entire content of which are hereby incorporated by the references.

Semi-crystalline polymers containing crystallizable side chains may be homopolymers or copolymers comprising from 50 percent to 100 percent by weight of units resulting from the polymerization of one or more monomers bearing a crystallizable hydrophobic side chain.

Particularly suitable examples of semi-crystalline polymers useful in this invention are described in U.S. Pat. No. 8,932,573, the entire content of which is hereby incorporated by the references.

Polymers bearing in the skeleton at least one crystallizable block are especially block copolymers consisting of at least two blocks of different chemical nature, one of which is crystallizable. Examples are block copolymers of olefin or of cycloolefin containing a crystallizable chain, and copolymers containing at least one crystallizable block, the rest of the copolymer being amorphous (at room temperature). These copolymers may also contain two crystallizable blocks of different chemical nature.

In particular, exemplary embodiments, the polymer comes from a crystallizable chain monomer selected from C14 to C30 saturated alkyl(meth)acrylates, including poly C10-30 alkyl(meth)acrylates.

Suitable examples of semi-crystalline alkyl(meth)acrylates include, but are not limited to, the Intelimer® or Doresco® products from the company Landec, such as those described in the brochure "Intelimer® Polymers" and/or are disclosed in U.S. patent application publication nos. 2006/0292095 and 2006/0263438, the disclosure of both of which is hereby incorporated by reference in their entirety. Specific examples include:

Doresco/Intelimer IPA 13-1®: polystearyl acrylate, with melting point of 49 degrees centigrade (° C.) and molecular weight (MW) of 145,000; and Doresco/Intelimer IPA 13-6®: polybehenyl acrylate, having melting point of 66 degrees centigrade (° C.) and molecular weight (MW) of 45,000-126,000 g/mol.

In accordance with the present invention, it is also possible to use the semi-crystalline polymers obtained by copolymerization of stearyl acrylate and of acrylic acid or of NVP, or by copolymerization of behenyl acrylate and of acrylic acid or NVP, as described in document U.S. Pat. No. 5,519,063 or EP-A-0 550 745, the entire contents of both of which are hereby incorporated by reference.

The at least one semi-crystalline polymer, poly C10-30 alkyl acrylate may be employed in the cosmetic composition of the present invention in an amount ranging from about 0.1 to about 20 percent by weight, or from about 0.5 to about 10 percent by weight, or from about 1 to about 5 percent by weight, relative to the total weight of the composition, including all ranges and subranges there between.

Applicable examples of semi-crystalline polymers useful in this invention are hyperbranched polymers, including hyperbranched functional polymer and these disclosed in US2015/0265519, the entire contents of which is hereby incorporated by the reference.

Generally, hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have any of the following: an extremely branched structure around a core; successive generations or layers of branching; layer of end chains.

According to this invention, particularly useful are Hyperbranched Polyacids.

In a preferred embodiment, the compositions of the invention comprise at least one hyperbranched polyacid. Hyperbranched polyacid refers to the fact the functional groups of the hyperbranched functional polymer are substituted with carboxylic acid groups.

The at least one hyperbranched polyacid compound of the present invention has at least two carboxyl groups. Preferably, the hyperbranched polyacid has a carboxyl number of at least 3, more preferably of at least 10, more preferably of at least 50, and more preferably of at least about 150. According to preferred embodiments, the at least one hyperbranched polyacid has a carboxyl number between 50 and 250, preferably between 75 and 225, preferably between 100 and 200, preferably between 125 and 175, including all ranges and subranges there between such as 90 to 150.

Suitable examples of hyperbranched polyacids can be found in U.S. Pat. No. 7,582,719 and US2013/0236409, the entire contents of which are hereby incorporated by reference.

In an embodiment the hyperbranched polyacid is a semi-crystalline polymer having a glass transition temperature (Tg) of from about −30° C. to about 0° C., particularly from about −20° C. to about −1° C., more typically from about −15° C. to about −5° C., and a melting point of from about 45° C. to about 100° C., typically from about 50° C. to about 90° C., most typically from about 55° C. to about 85° C.

A particularly preferred acid functional olefinic polymer is C30+ olefin/undecylenic acid copolymer available from New Phase Technologies under trade name Performa V™-6112.

The at least one hyperbranched polymer, in including at least one hyperbranched polyacid polymer may be present in the composition of the invention in an amount ranging from about 0.5% to about 10% by weight, more particularly from about 1% to about 8% by weight, most particularly from about 2% to about 6% by weight, including all ranges and subranges there between, relative to the total weight of the composition.

According to another embodiment of this invention, suitable semi-crystalline polymers are polyamide resins, as these disclosed in U.S. Pat. Nos. 8,715,634 and 7,871,634, the entire contents of which are hereby incorporated by the references.

Specifically, the disclosed polymers are ester-terminated polyamides represented by the following formula (I):

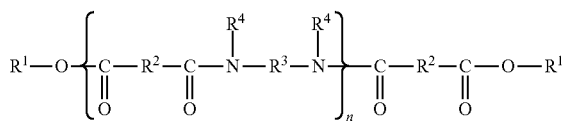

in which:

n is an integer which represents the number of amide units such that the number of ester groups present in the structuring polymer ranges from 10 percent to 50 percent of the total number of all the ester groups and all the amide groups comprised in the structuring polymer (e.g., n may be an integer ranging from 1 to 5, for example, an integer ranging from 3 to 5);

$R^1$, which are identical or different, are each chosen from alkyl groups comprising at least 4 carbon atoms and alkenyl groups comprising at least 4 carbon atoms (e.g., each can be chosen from C12 to C22 alkyl groups, such as from C16 to C22 alkyl groups);

$R^2$, which are identical or different, are each chosen from C4 to C42 hydrocarbon-based groups with the proviso that at least 50 percent of $R^2$ are chosen from C30 to C42 hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, C1 to C10 alkyl groups and a direct bond to group chosen from $R^3$ and another $R^4$ such that when the at least one group is chosen from another $R^4$, the nitrogen atom to which both $R^3$ and $R^4$ are bonded forms part of a heterocyclic structure defined in part by $R^4$—N—$R^3$, with the proviso that at least 50 percent of all $R^4$ are chosen from hydrogen atoms.

Non-limiting examples of at least one polyamide polymer that may be used in the compositions of the present invention include the commercial products sold by Arizona Chemical under the names UNICLEAR® 80 and UNICLEAR® 100. These are sold, respectively, in the form of an 80 percent (in terms of active material) gel in a mineral oil and a 100 percent (in terms of active material) gel.

Another example of the ester-terminated polyamides is commercially available from Arizona Chemical under the name UNICLEAR® VG (INCI Name: Ethylenediamine/stearyl dimer dilinoleate copolymer) and OLEOCRAFT™ from Croda (INCI Name) Ethylenediamine/stearyl dimer dilinoleate copolymer).

Waxes

As used herein, the term "wax" is understood to mean a lipophilic fatty compound, which is solid at room temperature and atmospheric pressure (760 mmHg, i.e. 10 Pa), which undergoes a reversible solid/liquid change of state, and which for instance has a melting point of greater than or equal to 30' C., for example, greater than or equal to 55' C., such as up to 120' C., which may be up to 250'C., such as up to 230' C.

By bringing the wax to its melting point, it is possible to make it miscible with the oils and to form a microscopically homogeneous mixture, but upon returning the temperature of the mixture to room temperature, the recrystallization of the wax in the oils of the mixture is obtained.

According to the present disclosure, the melting point values correspond to the melting peak measured using a differential scanning calorimeter (DSC), for example the Mettler, with a temperature rise of 5 or 10' C. per minute.

For the purposes of the present disclosure, the waxes may be those generally used in cosmetics or dermatology. They may be, for example, hydrocarbon-based waxes, silicone waxes and/or fluoro waxes, optionally comprising ester or hydroxyl functional groups. They may also be of natural or synthetic origin.

Non-limiting illustrations of the waxes that may be used may be made of: beeswax, lanolin wax and Chinese insect waxes; rice wax, carnauba wax, candelilla wax, ouricury wax, cork fiber wax, sugarcane wax, Japan wax and sumach wax; montan wax; microcrystalline waxes, paraffin waxes, ozokerites, ceresin wax, lignite waxes, polyethylene waxes, the waxes obtained by Fisher-Tropsch synthesis, and fatty acid esters and glycerides that are solid at 40' C. and above, for example, above 55' C., The waxes obtained by catalytic hydrogenation of animal or plant oils comprising linear and branched C8-C» fatty chains, such as hydrogenated jojoba oil, hydrogenated sunflower oil, hydrogenated castor oil, hydrogenated coconut oil and hydrogenated lanolin oil, silicone waxes or fluoro waxes, and mixtures thereof.

The total amount of at least one oil phase thickener in the cosmetic composition can vary but is typically about 0.2, 0.3, 0.4, 0.5, 0.6, 0.7, 0.8, 0.9, 1.0 to about 1.0, 1.2, 1.4, 1.6, 1.8, 1.9, 2.0, 2.1, 2.2, 2.3, 2.4 or 2.5 wt. %, based on the total weight of the composition.

Emulsifier System

The emulsifier system is comprised of at least one anionic surfactant, at least one nonionic surfactant having an HLB of greater than or equal to about 14.0, and at least one nonionic surfactant having an HLB from about 1.0 to about 5.0, wherein the combined HLB of the surfactants is from about 9.0 to about 13.0.

Suitable anionic surfactants for use in the present invention include, but are not limited to:

alkali metal salts of cetyl phosphate;
alkali metal salts of dicetyl phosphate and of dimyristyl phosphate;
alkali metal salts of cholesterol sulphate;
alkali metal salts of cholesterol phosphate;
lipoamino acids and their salts, such as mono and disodium acylglutamates, for instance the disodium salt of N-stearoyl-L-glutamic acid sold under the trade name AMISOFT® HS 21 P by the company Ajinomoto;
sodium salts of phosphatidic acid;
phospholipids;
alkylsulphonic derivatives, in particular of formula (I):

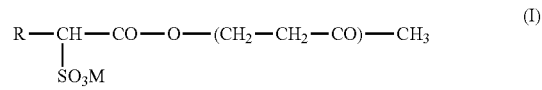

in which R represents C16-C22 alkyl radicals, in particular the C16H33 and C18H37 radicals taken as a mixture or separately, and M is an alkali metal or alkaline earth metal, such as sodium; and mixtures thereof.

In one embodiment, the anionic surfactant is potassium cetyl phosphate.

Particularly preferred anionic surfactants are sodium stearoyl glutamate and disodium stearoyl glutamate.

The anionic surfactant will typically be employed in an amount of from about 0.1 to about 2 wt. % based on the total weight of the composition.

The total amount of at least one anionic surfactant in the cosmetic composition can vary but is typically about 0.1, 0.2, 0.3, 0.4, 0.5, 0.6, 0.7, 0.8, 0.9, 1.0 to about 1.0, 1.2, 1.4, 1.6, 1.8, 1.9, or 2.0 wt. %, based on the total weight of the composition.

Suitable nonionic surfactants having an HLB greater than or equal to about 14.0 include, but are not limited to Polyoxyethylene fatty acid esters and mixtures thereof.

In some embodiments, the at least nonionic surfactant having an HLB of greater than or equal to about 14.0 is chosen from Polysorbate 60 NF (HLB=14.9), Polysorbate 60 (HLB=14.9), Polysorbate 80 (HLB=15), Isosteareth-20 (HLB=15), PEG-60) Almond Glycerides (HLB=15), Polysorbate 80 NF(HLB=15), PEG-20 Methyl Glucose Sesquistearate (HLB=15), Ceteareth-20 (HLB=15.2), Oleth-20 (HLB=15.3) Steareth-20 (HLB=15.3), Steareth-21 (HLB=15.5), Ceteth-20 (HLB=15.7), Isoceteth-20 (HLB=15.7), Polysorbate 20 (HLB=16.7), Polysorbate 20 NF (HLB=16.7) Laureth-23 (HLB=16.9) PEG-100 Stearate (HLB=18.8) Steareth-100 (HLB=18.8), PEG-80 Sorbitan Laurate (HLB=19.1) and mixtures thereof.

A particularly preferred Polyoxyethylene fatty acid esters is PEG-100 stearate.

The at least one nonionic surfactant having an HLB of greater than or equal to about 14.0 will typically be employed in an amount of from about 0.2 to about 2.5% by weight The total amount of at least one nonionic surfactant in the cosmetic composition can vary but is typically from about 0.2, 0.3, 0.4, 0.5, 0.6, 0.7, 0.8, 0.9, 1.0 to about 1.0, 1.2, 1.4, 1.6, 1.8, 1.9, 2.0, 2.1, 2.2, 2.3, 2.4 or 2.5 wt. %, based on the total weight of the composition.

Suitable nonionic surfactants having an HLB from about 1.0 to about 5.0 include, but are not limited to, Glycol Distearate (HLB=1), Sorbitan Trioleate (HLB=1.8), Propylene Glycol Isostearate (HLB=2.5), Glycol Stearate (HLB=2.9), Sorbitan Sesquioleate (HLB=3.7), Glyceryl Stearate (HLB=3.8), Lecithin (HLB=4), Sorbitan Oleate (HLB=4.3), Sorbitan Monostearate NF (HLB=4.7), Sorbitan Stearate (HLB=4.7), Sorbitan Isostearate (HLB=4.7), Steareth-2 (HLB=4.9), Oleth-2 (HLB=4.9). The HBL value can vary from about 1.0, 1.2, 1.4, 1.6, 1.8, 2.0, 2.1, 2.2, 2.3, 2.4, 2.5 to about 2.5, 2.6, 2.7, 2.8, 2.9, 3.2, 3.4, 3.6, 3.8, 4.0, 4.2, 4.4, 4.6, 4.8 or 5.0.

Particularly preferred nonionic surfactants having an HLB from about 1 to about 5 include Glyceryl Stearate.

The total amount of at least one nonionic surfactant having an HLB from about 1.0 to about 5.0 in the cosmetic composition can vary but will be typically employed in an amount from about 0.2, 0.3, 0.4, 0.5, 0.6, 0.7, 0.8, 0.9, 1.0 to about 1.0, 1.2, 1.4, 1.6, 1.8, 1.9, 2.0, 2.1, 2.2, 2.3, 2.4 or 2.5 wt. %, based on the total weight of the composition.

The emulsifier system will typically be present in the composition in an amount of about 1.0, 1.2, 1.4, 1.6, 1.8, 2.0, 2.2, 2.4, 2.6, 2.8 to about 2.8, 3.0, 3.2, 3.4, 3.6, 3.8, 4.0, 4.2, 4.4, 4.6, 4.8 or 5 wt. % based on the total weight of the composition.

Organic UV Filters

UV filters are well known in the art for their use in protection from UV radiation. Non-limiting examples of organic UV filters include para-aminobenzoate derivative, a salicylate derivative, a cinnamate derivative, a benzophenone or an aminobenzophenone derivative, an anthranillate derivative, a β,β-diphenylacrylate derivative, a benzylidenecamphor derivative, a phenylbenzimidazole derivative, a benzotriazole derivative, a triazine derivative, a bisresorcinyl triazine derivative, an imidazoline derivative, a benzylmalonate derivative, a 4,4-diarylbutadiene derivative, a benzoxazole derivative, a merocyanine derivative, a malonitrile or a malonate diphenyl butadiene derivative, a chalcone derivative, and mixtures thereof. It is common to include a plurality of organic UV filters, i.e., two or more organic UV filters. It is also useful to include at least one organic UVA filter (e.g., avobenzone) and at least one organic UVB filter.

The composition may include any suitable amount of one or more UV filters. In one embodiment, the composition includes about 10 to about 40% by weight based on the total weight of the composition.

The one or more UV filters may include any suitable UV filter or UV filter system, including, but not limited to, solid organic lipsoluble UV filters, such as, but not limited to, butyl methoxydibenzoylmethane, and ethylhexyl trazone, liposoluble organic UV filters, such as, but not limited to, cinnamate compounds, anthranilates, salicylate compounds, dibenzoylmethane compounds, such as avobenzone, camphor compounds, 13,13-diphenylacrylate compounds, triazine compounds, benzotriazole compounds, benzalmalonate compounds (particularly those cited in U.S. Pat. No. 5,624,663), imidazoline compounds, p-aminobenzoate compounds (PABA), benzoxazole compounds (as described in patent applications EP0832642, EP1027883, EP1300137, and DE10162844), UV-filter polymers and UV-filter silicones (as described in patent application WO-93/04665), α-alkylstyrene dimers (as described in patent application DE19855649), 4,4-diarylbutadiens (as described in patent applications EP0967200, DE19746654, DE19755649, EP-A-1008586, EP1133980, and EP133981), merocyanine (as described in U.S. Pat. No. 4,195,999, WO2004/006878, WO2008/090066, WO2011113718, WO2009027258, and the documents IP COM JOURNAL No 000179675D published on Feb. 23, 2009, IP COM JOURNAL No 000182396D published on Apr. 29, 2009, IP COM JOURNAL No 000189542D published on Nov. 12, 2009, IP COM Journal No IPCOM000011179D published on Mar. 4, 2004), and their mixtures. The above documents are incorporated by reference in their entirety.

By way of non-limiting example, at least one UV filter or UV filter system may include (listed by INCI name): dibenzoylmethane compounds such as butylmethoxydibenzoylmethane (for example, as sold under the trade name Parsol 1789® by DSM Nutritional Products, Inc.) and isopropyldibenzoylmethane; para-aminobenzoic compounds such as ethyl PABA, ethyl dihydroxypropyl PABA, ethylhexyl dimethyl PABA (sold under the name ESCALOL 507® by ISP), and glyceryl PABA; salicylic derivatives such as homosalate (sold under the commercial name Eusolex HMS by Rona/EM Industries) and ethylhexyl salicylate (sold under the commercial name NEO HELIOPAN OS by SYMRISE); cinnamic derivatives such as ethylhexyl methoxycinnamate (sold under the commercial name PARSOL MCX by DSM NUTRITIONAL PRODUCTS), isopropyl methoxy cinnamate, isoamyl methoxy cinnamate (sold under the commercial name NEO HELIOPAN E 1000 by SYMRISE), and cinoxate, diisopropyl methylcinnamate; derivatives of β,β-diphenylacrylate such as octocrylene (sold under the commercial name UVINUL N539 by BASF) and etocrylene (sold under the commercial name UVINUL N35 by BASF); and hexyl 2-(4-diethylamino-2-hydroxybenzoyl) benzoate (sold under the commercial name UVINUL A Plus or in the form of a mixture with octylmethoxycinnamate under the commercial name UVINUL A+B by BASF); benzylidenecamphor derivatives such as 3-Benzylidene camphor (manufactured under the commercial name MEXORYL SD by CHIMEX), 4-Methylbenzylidene camphor (sold under the commercial name EUSOLEX 6300 by MERC), and polyacrylamidomethyl benzylidene camphor (manufactured under the commercial name MEXORYL SW by CHIMEX); phenyl benzotriazole derivatives such as drometrizole trisiloxane (sold under the commercial name Silatrizole by RHODIA CHIMIE); triazine derivatives such as bis-ethylhexyloxyphenol methoxyphenyl triazine (sold under the commercial name TINOSORB S by BASF), ethylhexyl triazone (sold under the commercial name UVINUL T150 by BASF), diethylhexyl butamido triazone (sold under the commercial name UVASORB HEB by SIGMA 3V), 2,4,6-tris(4'-amino benzalmalonate de dinéopentyle)-s-triazine, 2,4,6-tris-(diisobutyle-4'-amino benzalmalonate)-s-triazine, and 2,4-bis (dinéopentyle-4'-aminobenzalmalonate)-6-(4'-aminobenzoate de n-butyle)-s-triazine; triazine silicones substituted by two aminobenzoates groups such 2,4-bis-(n-butyl 4'-aminobenzalmalonate)-6-[(3-{1,3,3,3-tetramethyl-1-[(trimethyl-silyloxy]-disiloxanyl}propyl)amino]-s-triazine (and others as described in the patent EP0841341); anthranilic derivatives such as menthyl anthranilate (sold under the commercial name NEO HELIOPAN MA by SYMRISE), imidazoline derivatives such as ethylhexyl dimethoxybenzylidene dioxoimidazoline propionate; benzalmalonate derivatives such as di-neopentyl 4'-methoxybenzalmalonate and polyorganosiloxane with benzalmalonate functions such as Polysilicone-15 (sold under the commercial name PARSOL SLX by DSM NUTRITIONAL PRODUCTS); derivatives of 4,4-diarylbutadiene such as 1,1-dicarboxy (2,2'-dimethyl-propyl)-4,4-diphenylbutadiene; benzoxazole derivatives such as 2,4-bis-[5-1(dimethylpropyl)benzoxazol-2-yl-(4-phenyl)-imino]-6-(2-ethylhexyl)-imino-1,3,5-triazine (sold under the commercial name Uvasorb K2A by Sigma 3V); lipophilic merocyanine derivatives such as Octyl-5-N,N-diethylamino-2-phenysulfonyl-2,4-pentadienoate; terephthalylidene dicamphor sulfonic acid (Sold under the commercial name Mexoryl SX by CHIMEX; and drometrizole trisiloxane (Sold under the commercial name Mexoryl XL by RHODIA).

In one embodiment, one or more UV-A filter is avobenzone and one or more one UV-B filter includes, consists essentially of or consists of octisalate, octocrylene, and homosalate. In another embodiment, the UV-A filter is avobenzone and the UV-B filter includes, consists essentially of or consists of at least two of octisalate, octocrylene, and homosalate. In still another embodiment, the UV filter system including the UV-A and the UV-B filters includes, consists essentially of or consists of each of avobenzone, octisalate, octocrylene, and homosalate.

Active Agents

Sunscreen compositions according to the present disclosure can optionally further include active agents. Suitable active agents include, for example, anti-acne agents, antimicrobial agents, anti-inflammatory agents, analgesics, antierythemal agents, antiruritic agents, antiedermal agents, antipsoriatic agents, antifungal agents, skin protectants, vitamins, antioxidants, scavengers, antiirritants, antibacterial agents, antiviral agents, antiaging agents, photo protection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self-tanning agents, coenzyme Q10, niacinimide, capcasin, caffeine, and any combination of any of the foregoing.

Adjuvants

Sunscreen compositions according to the present disclosure can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Suitable conditioning agents include, but are not limited to, cyclomethicone; petrolatum; dimethicone; dimethiconol; silicone, such as cyclopentasiloxane and diisostearoyl trimethylolpropane siloxy silicate; sodium hyaluronate; isopropyl palmitate; soybean oil; linoleic acid; PPG-12/saturated methylene diphenyldiisocyanate copolymer; urea; amodimethicone; trideceth-12; cekimonium chloride; diphenyl dimethicone; propylene glycol; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, phenoxyethanol, methylparaben, ethylparaben, propylparaben, phytic acid, imidazolidinyl urea, sodium dehydroacetate, benzyl alcohol, methylehloroisothiazolinone, methylisothiazolinone, and any combination thereof. The sunscreen composition generally contains from about 0.001% to about 20% by weight of preservatives, based on 100% weight of total sunscreen composition and heat-protective composition. In another aspect, the composition contains from about 0.1% to about 10%.

Cosmetically Acceptable Carrier

The sunscreen compositions include a cosmetically acceptable carrier. The phrase "cosmetically acceptable" means that the material is compatible with skin. For example, "cosmetically acceptable carrier" means a carrier that is compatible with skin and acceptable for application to the skin of the body, especially the skin of the face.

The cosmetically acceptable carrier may include, for example, water and/or water soluble solvents. Non-limiting examples of cosmetically acceptable carriers include glycerin, C1-4 alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

The above lists are only examples and not limiting.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

The term "HLB" refers to hydrophilic-lipophilic balance, which is a measure of the degree to which a surfactant is hydrophilic or lipophilic. The term "combined HLB" is used herein to refer to the total hydrophilic-lipophilic balance of all emulsifiers (or combinations of emulsifiers) in the formula. Both "HLB" and "combined HLB" are determined via methods described in Griffin, W. C. "Classification of Surface Active Agents by HLB" *J. Soc. Cosmet. Chem.*, 1949, 1, 311-326 and Griffin, W. C. "Calculation of HLB values of Nonionic Surfactants", *J. Soc. Cosmet. Chem.*, 1954, 5, 249-256.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

EXAMPLES

The following Examples are provided for illustrative purposes only, and are not intended to be limiting.

Example 1

Sunscreen compositions were studied. Details for the sunscreen compositions are provided in Table 1 below.

TABLE 1

| | | | Inventive Examples | | |
|---|---|---|---|---|---|
| Phase | Claims | Function | | Inventive Ex. 1 | Inventive Ex. 2 |
| A1 | a | Film former | POLYURETHANE-35 | 1.8245 | 1.8245 |
| B1 | b | Oil phase thickeners | ETHYLENEDIAMINE/STEARYL DIMER DILINOLEATE COPOLYMER | 1 | |
| | | | HYDROGENATED CASTOR OIL | 1 | |
| B2 | c | Surfactants | GLYCERYL STEARATE | 0.65 | 0.65 |
| B2 | | | PEG-100 STEARATE | 0.65 | 0.65 |
| B2 | | | STEARIC ACID | 1.5 | 1.5 |
| A1 | | | POTASSIUM CETYL PHOSPHATE | 1 | 1 |
| B2 | | Emollients | DIISOPROPYL SEBACATE, C12-15 ALKYL BENZOATE, BUTYROSPERMUM PARKII (SHEA) BUTTER/BUTYROSPERMUM PARKII BUTTER | 7.1 | 7.1 |
| B1 | | Sun Filters | OCTOCRYLENE, HOMOSATE, ETHYLHEXYL TRIAZONE, BIS-ETHYLHEXYLOXYPHENOL METHOXYPHENYL TRIAZINE, ETHYLHEXYL SALICYLATE, DROMETRIZOLE TRISILOXANE, BUTYL METHOXYDIBENZOYLMETHANE | 28.5 | 28.5 |
| A1 | | Solvent | WATER | 47.2 | 47.2 |
| B2 | | Water soluble solvent | CAPRYLYL GLYCOL ALCOHOL DENAT. GLYCERIN C12-15 ALKYL BENZOATE | 12.4 | 0.4 |
| B2 | | Preservative | PHENOXYETHANOL | 0.7 | 0.7 |

TABLE 1-continued

Inventive Examples

| Phase | Claims | Function | | Inventive Ex. 1 | Inventive Ex. 2 |
|---|---|---|---|---|---|
| A1 | | Active Compound | TRIETHANOLAMINE; DISODIUM EDTA | 0.44 | 0.44 |

In making the formulation in the above table, the following procedure was used.
1. The Raw Materials of phase A were dissolved at 65 C.
2. The Raw Materials of phase B1 and B2 were dissolved at 65 C.
3. The phase B1 and B2 were added to phase A under homogenizing for 15 min.
4. The homogenizer was removed and the solution was brought back to normal stirring.
5. Then phase C was added to dilute the system.
6. After cooling down to under 30 C, phase D was added to the system.

Example 2

Film Formers and Oil Phase Thickener Evaluation

Several film formers as well as several oil phase thickeners were studied in order to evaluate the in-vitro SPF and in-vitro Water Resistance (WR) once incorporated in the compositions of the instant disclosure.

The results are presented in the Table below. The inventive and comparatives examples presented in Table 2 were prepared according to the procedure described in Example 1.

TABLE 2

In-Vitro Evaluation of film formers and oil thickeners (organic filters only)

| Examples | Film former | Oil phase thickener | In-vitro SPF* | in-vitro WR** | sensory evaluation*** |
|---|---|---|---|---|---|
| Comparative Ex. 1 | None | None | 29.35 | 71% | 3 |
| Comparative Ex. 2 | polyurethane-35 in 2% | None | 46.11 | 82% | 1 |
| Comparative Ex. 3 | silicone acrylate emulsion 2% | None | 32 | 43% | N/A**** |
| Comparative Ex. 4 | hydrocarbon dimer in 2% | None | 26 | 34% | N/A**** |
| Comparative Ex. 5 | polyurethane-35 in 3% | None | 46.2 | 121% | 1 |
| Comparative Ex. 6 | None | hydrogenated castor oil in 3% | 31.73 | 110% | 2.5 |
| Inventive Ex. 1 | polyurethane-35 in 2% | ethylenediamine/stearyl dimer dilinoleate copolymer in 1% | 46.37 | 130% | 2.5 |
| Inventive Ex.2 | polyurethane-35 in 2% | hydrogenated castor oil in 1% | 43.34 | 86% | 2.5 |

*SPF = Sun Protection Factor
**WR = Water Resistance
***= sensory evaluation scale = 1 is the worst and 3 is the best
****NA = Non-Available Experimental Procedure In vitro SPF and in vitro WR was measured for sunscreen formulations using a method adapted from Fageon, L. et al. Int. J. Cosmetic Sci., 2009, 405-17 and Pissavini, M. et al. *Int. J. Cosmetic Sci.*, 2007, 29, 451-60. Samples weighing 30 mg were transferred by an adjustable pipette and uniformly applied to a Schonberg sand-blasted PMMA (polymethyl methacrylate) plates (roughness 6 µm, 5 cm by 5 cm dimensions). The sample was uniformly applied to the plate with a finger inside a fingercot using a series of circular motions followed by side-to-side motions in a regular and controlled fashion such that the amount of product remaining on the plate following application described in this manner weighed approximately 15-20 mg. The plate was dried at room temperature for 15 to 20 minutes and the in vitro SPF was measured using a Labsphere Ultraviolet Transmittance Analyzer (Model UV-2000 available from the Solar Light Company, Philadelphia, Pa.). Each measurement was made 5 times (5 times on each plate) on 3 plates for each composition. The SPF of each plate was recorded as an average of 5 measurements over different areas of the plate. The SPF of each formulation was recorded as an average of the three plates. This SPF values were recorded as the in-vitro SPF and also SPF initial (SPFi) for each formula. Then the plates were immersed into DI water for 40 mins under stirring at 25 rpm at room temperature by using a dissolution apparatus. After being immersed for 40 min, the plates were extracted and dried for 15-20 min at room temperature. Then, the final SPF value (SPFf) after immersion were measured using labsphere according to the same procedure as described above. The in-vitro water resistance value (in vitro WR) was then calculated using the equation as follows:

In vitro WR=(SPF$i$−1)/(SPF$f$−1)×100%

SPFi=SPF initial

SPFf=SPF after immersion for 40 min.

The sensory evaluation of inventive and comparative formulas was completed by applying sunscreen formulas on forearms of 5 subjects. The sunscreen was applied in amount of 2 mg/cm$^2$, and each formula was evaluated for spreading, tackiness, absorbance, feel on skin immediately after application and feel on skin after drying for 5 or more minutes. Each attribute was rated individually and an overall score representing "sensory evaluation" was established on a 1 to 3 scale, with 1 representing the worst sensory overall and 3 representing the best sensory overall.

Results

It was observed that the nature of the film formers as well as the nature of the oil phase thickeners were crucial in order to improve simultaneously the in-vitro SPF, the in-vitro WR and the sensorial feeling of the compositions.

In order to evaluate the performance of the association of the film former and oil phase thickener, a control was first tested (Comparative Example 1, Table 2). Comparative Example 1 did not contain any film former or oil phase thickener. It was observed that the in-vitro SPF was 29.35, the in-vitro WR was 70.6% and the sensorial effect of the composition was the best (evaluation scale of 3). First, different film formers were tested and added to Comparative Example 1 without changing anything else. It was observed that not every film former were equals. The addition of Polyurethane-35 at 2% (comparative Example 2) without any oil phase thickener showed an improvement in term of SPF (46.11) as well as an improvement of the WR. Nonetheless, the sensorial feeling of the composition was bad (evaluation scale of 1). But, when film formers such as silicone acrylate at 2% (Comparative Example 3) and hydrocarbon dimer at 2% (Comparative Example 4) were added, the in-vitro SPF and in-vitro WR were not significantly improved compared to Comparative Example 2. The nature of the film formers seemed to be important as well as the concertation. Indeed, in Comparative Example 5 (Polyurethane-35 at 3%), we observed an increase of the in-vitro SPF (46.2), a boost of the in-vitro WR (120.6%). But then, the sensorial feeling was bad and evaluated at 1. After testing the film formers, an oil phase thickener was tested with Comparative Example 6 (hydrogenated castor oil 3%). In this case, the in-vitro SPF increased a little bit (31.73), a boost of the in-vitro WR was observed (110%) as well as an improvement of the sensory (Scale 2.5). The next step was to test the combination of polyurethane-35 at 2% with a certain type of oil phase thickeners such as ethylenediamine/stearyl dimer dilinoleate copolymer at 1% (Inventive Example 1) or hydrogenated castor oil at 1% (Inventive Example 2). A great boost of in-vitro SPF (46.37 and 43.34, respectively), of in-vitro WR (126.70% and 83.36%, respectively) as well as a good improvement of the sensory (scale of 2.5 in both examples) was observed.

These results allowed to conclude that the association of certain types of film formers with certain types of oil phase thickeners within a certain concentration were able to improve the SPF values, the Water Resistance and the sensorial feeling of the oil-in-water cosmetic composition described in the instant disclosure.

Example 3

UV System Evaluation

Organic and UV filters were evaluated. The results are presented in the Table below. The inventive and comparatives examples presented in Table 3 were prepared according to the procedure described in Example 1.

TABLE 3

| | In-Vitro Evaluation of organic UV filters and mineral UV filters | | | | |
|---|---|---|---|---|---|
| Examples | Organic UV Filter System (%) | Mineral UV Filter System (%) | Film former and oil thickeners | In-vitro WR | In-vivo WR |
| Comparative Ex. 7 | 17.7% | 6% | polyurethane-35 in 2% + ethylenediamine/stearyl dimer dilinoleate copolymer in 1% | 89.21% | 63% |
| Comparative Ex. 8 | 34% | 4% | polyurethane-35 in 2% + ethylenediamine/stearyl dimer dilinoleate copolymer in 1% | 49.98% | 58.60% |
| Inventive Ex. 1 | 28.5% | 0% | polyurethane-35 in 2% + ethylenediaminehtearyl dimer dilinoleate copolymer in 1% | 126.70% | 110.80% |

Results

It was observed that the nature of the UV filters was crucial in order to improve in-vitro WR without compromising the SPF and the sensory.

According to Table 3, surprisingly, the compositions containing only of organic UV filters exhibited a much better Water Resistance (in-vitro 126.70% and in-vivo 110.80%) than when the compositions contained a mixture of organic and mineral UV filters (see Comparative Examples 7 and 8)

Example 4

Emulsifier System Evaluation

Different emulsifier systems were evaluated. The results are presented in Table 4 below. The inventive and comparatives examples presented in Table 4 were prepared according to the procedure described in Example 1.

TABLE 4

| | Comparison of emulsifier systems | | |
|---|---|---|---|
| Examples | Emulsifier System | Film formers | In-vitro WR |
| Comparative Ex. 9 | polysorbate 60, polysorbate 61, disodium stearoyl glutamate stearic acid, glyceryl stearate | polyurethane-35 2% | 33% |
| Inventive Ex. 1 | PEG-100 stearate, potassium cetyl phosphate | polyurethane-35 2% | 127% |

Results

It was observed that the selection of the emulsifier system was very important in order to observe a significant improvement of the in vitro WR.

According to Table 4, surprisingly, the compositions containing stearic acid, glyceryl stearate PEG-100 stearate, potassium cetyl phosphate exhibited a much better Water Resistance (in-vitro 127%) than when the compositions contained a different emulsifier system such as polysorbate 60, polysorbate 61, disodium stearoyl glutamate (see Comparative Example 9).

The foregoing description illustrates and describes the disclosure. Additionally, the disclosure shows and describes only the preferred embodiments and is capable of changes or modifications within the scope of the inventive concepts expressed herein, commensurate with the above teachings and/or the skill or knowledge of the relevant art. The embodiments described herein are intended to explain best modes and to enable others skilled in the art to utilize the disclosure in such, or other, embodiments and variations. Accordingly, the description is not intended to limit the invention. Also, it is intended that the appended claims are construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, E, F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a fatty acid may be considered both an emulsifier and a fatty compound. If a particular composition includes both an emulsifier and a fatty compound, a single fatty acid will serve as only the emulsifier or only the fatty compound (the single fatty acid does not serve as both the emulsifier and the fatty component).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto the surface of keratinous substrates such as skin, in particular, the skin of the head, face, and neck.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. An oil-in-water sunscreen cosmetic composition comprising:
   a. From about 1 to about 5 wt. % of at least one film former selected from the group consisting of polyurethane 32, polyurethane-34, polyurethane-35, polyurethane-48, and a mixture thereof;
   b. From about 0.2 about 2 wt. % of at least one oil phase thickener selected from Ethylenediamine/Stearyl Dimer Dilinoleate Copolymer, Hydrogenated Castor Oil, Synthetic Oils, Hydrogenated Palm Oil, Hydrogenated Coconut Oil, waxes and mixture thereof;
   c. An emulsifier system comprising:
      i. At least one anionic surfactant;
      ii. At least one nonionic surfactant having an HLB of greater than or equal to about 14.0; and
      iii. At least one nonionic surfactant having an HLB from about 1.0 to about 5.0; and
   wherein the combined HLB of the surfactants is from about 9.0 to about 13.0;
   d. one or more organic UV filters selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and mixture thereof;

wherein the combination of the at least one film former and the at least one oil phase thickener improves the water resistance of the composition and improves SPF of the composition once applied on the skin; and wherein the weight percentages are based on the total weight of the composition.

2. The composition of claim 1, wherein the at least one film former is present from about 1.0 to about 3.5 wt. % based on the total weight of the composition.

3. The composition of claim 1, wherein the oil phase thickener is about 0.8 to about 1.5 wt. % based on the total weight of the composition.

4. The composition of claim 1, wherein the at least one anionic surfactant is chosen from alkali metal salts of potassium cetyl phosphate, dicetyl phosphate and of dimyristyl phosphate; alkali metal salts of cholesterol sulphate; alkali metal salts of cholesterol phosphate; lipoamino acids and their salts; sodium salts of 5 phosphatidic acid; phospholipids; alkylsulphonic derivatives; and mixtures thereof.

5. The composition of claim 4, wherein the lipoamino acids and their salts are selected from the group consisting of sodium stearoyl glutamate or disodium stearoyl glutamate.

6. The composition of claim 1, wherein the at least one anionic surfactant is potassium cetyl phosphate.

7. The composition of claim 1, wherein the at least one nonionic surfactant having an HLB of greater than or equal to about 14.0 is selected from the group consisting of Polyoxyethylene fatty acid esters or mixtures thereof.

8. The composition of claim 7, wherein the polyoxyethylene fatty acid esters is PEG-100 Stearate.

9. The composition of claim 1, wherein the at least one nonionic surfactant having an HLB from about 1.0 to about 5.0 is selected from the group consisting of Glycol Distearate, Sorbitan Trioleate, Propylene Glycol Isostearate, Glycol Stearate, Sorbitan Sesquioleate, Glyceryl Stearate, Lecithin, Sorbitan Oleate, Sorbitan Monostearate NF, Sorbitan Stearate, Sorbitan Isostearate, Steareth-2, Oleth-2 and mixtures thereof.

10. The composition of claim 9, wherein the at least one nonionic surfactant having an HLB from about 1.0 to about 5.0 is Glyceryl Stearate.

11. An oil-in-water sunscreen cosmetic composition comprising:
 a. From about 1.0 to about 3.5 wt. % of at least one film former selected from the group consisting of polyurethane 32, polyurethane-34, polyurethane-35, polyurethane-48, and a mixture thereof;
 b. From about 0.2 to about 2.0 wt. % of at least one oil phase thickener selected from the group consisting of Ethylenediamine/Stearyl Dimer Dilinoleate Copolymer, Hydrogenated Castor Oil, Synthetic Oils, Hydrogenated Palm Oil, Hydrogenated Coconut Oil, waxes and mixture thereof;
 c. An emulsifier system comprising:
  i. From about 0.1% to about 2% of at least one anionic surfactant;
  ii. From about 0.5% to about 2.0% of at least one nonionic surfactant having an HLB of greater than or equal to about 14.0; and
  iii. From about 0.5% to about 2% of at least one nonionic surfactant having an HLB from about 1.0 to about 5.0; and
  wherein the combined HLB of the surfactants is from about 9.0 to about 13.0;
 d. one or more organic UV filters selected from the group consisting of a para-aminobenzoic acid derivative, a salicylic derivative, a cinnamic derivative, a benzophenone or an aminobenzophenone, an anthranillic derivative, a β,β-diphenylacrylate derivative, a benzylidenecamphor derivative, a phenylbenzimidazole derivative, a benzotriazole derivative, a triazine derivative, a bisresorcinyl triazine, an imidazoline derivative, a benzalmalonate derivative, a 4,4-diarylbutadiene derivative, a benzoxazole derivative, a merocyanine, malonitrile or a malonate diphenyl butadiene derivative, a chalcone, and mixture thereof;
wherein the combination of the at least one film former and the at least one oil phase thickener improves the water resistance of the composition, and improves SPF of the composition once applied on the skin; and
wherein the weight percentages are based on the total weight of the composition.

12. The composition of claim 1, wherein the oil-in-water cosmetic composition is water resistant.

13. A method for protecting skin from UV radiation comprising applying an effective amount of the composition of claim 1 to the skin.

* * * * *